United States Patent [19]

Matsui et al.

[11] 3,954,811
[45] May 4, 1976

[54] PRODUCTION OF CYCLOPENTANE DERIVATIVES

[75] Inventors: Masanao Matsui, Tokyo; Junki Katsube, Toyonaka; Eichi Murayama, Tokarazuka, all of Japan

[73] Assignee: Sumitomo Chemical Co., Ltd., Osaka, Japan

[22] Filed: May 30, 1974

[21] Appl. No.: 474,628

Related U.S. Application Data

[62] Division of Ser. No. 70,877, Sept. 9, 1970, Pat. No. 3,832,380.

[30] Foreign Application Priority Data

Sept. 9, 1969 Japan.................. 44-71785
Nov. 18, 1969 Japan.................. 44-92746
Nov. 18, 1969 Japan.................. 44-92747
Jan. 31, 1970 Japan.................. 45-8670

[52] U.S. Cl.................. 260/345.7; 260/345.8; 260/404; 260/404.5; 260/464

[51] Int. Cl.[2].............. C07D 309/00; C07C 120/00; C07C 120/06; C07C 121/46

[58] Field of Search..... 260/464, 404, 395, 448.8 R, 260/345.7, 345.8, 465 D

[56] References Cited
UNITED STATES PATENTS

| | | | |
|---|---|---|---|
| 3,432,541 | 3/1969 | Bagli et al.................. | 260/464 X |
| 3,444,161 | 5/1969 | Nagata........................ | 260/464 X |
| 3,445,502 | 5/1969 | Brown et al.................. | 260/464 X |
| 3,506,693 | 4/1970 | Bucourt et al................ | 260/464 X |
| 3,806,535 | 4/1974 | Sakai et al................... | 260/464 X |
| 3,810,943 | 5/1974 | Jones et al................... | 260/464 X |
| 3,836,581 | 9/1974 | Bernady et al................ | 260/464 X |

*Primary Examiner*—Joseph P. Brust
*Attorney, Agent, or Firm*—Sughrue, Rothwell, Mion, Zinn & Macpeak

[57] ABSTRACT

A process for producing cyclopentane derivatives of the formula

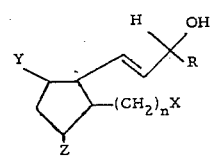

wherein R is hydrogen or a $C_1$ to $C_6$ alkyl group, X is a carboxyl or a carboalkoxy group, and the like; Y and Z each is a hydroxyl group, and the like; and n is an integer of from 5 to 7. The derivatives are useful as medicines. The process of this invention comprises the steps shown in the following reaction scheme:

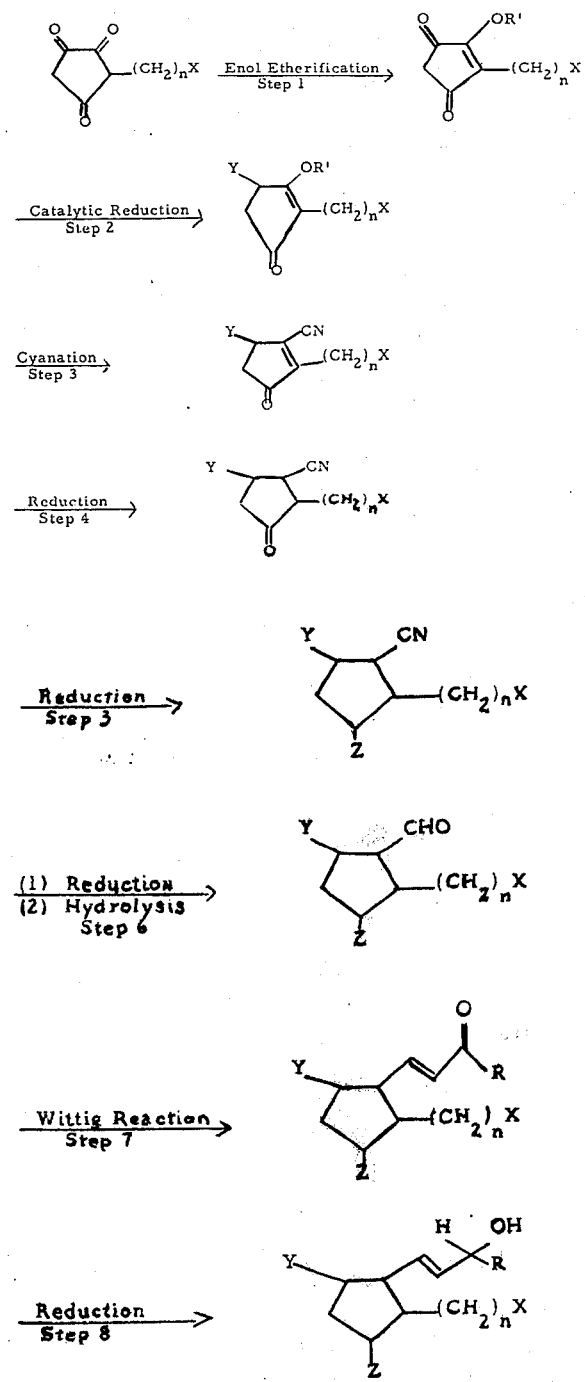

wherein R, X, Y, Z and n are as defined above, and wherein R' is lower alkyl group.

4 Claims, No Drawings

PRODUCTION OF CYCLOPENTANE DERIVATIVES

This is a divisional application of Ser. No. 70,877, filed Sept. 9, 1970, now U.S. Pat. No. 3,832,380.

BACKGROUND OF THE INVENTION

The present invention relates to a process for the production of cyclopentane derivatives. More particularly, the present invention relates to a novel process for producing 3-hydroxyalkenyl-cyclopentane-1,4-diol derivatives having the formula

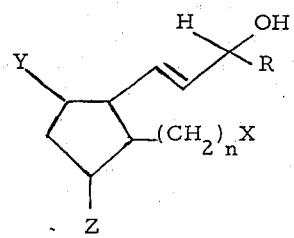

wherein R represents hydrogen or a $C_1$ to $C_6$ alkyl group; wherein X represents a carboxyl group or its homologue, wherein Y and Z each represents a hydroxyl group or its homologue, and wherein $n$ represents an integer of from 5 to 7.

The cyclopentane derivatives produced by the process of this invention are useful as medicines or intermediates for the production of medicines. These derivatives include the prostaglandins, the prostate hormones and their homologues, and have broad pharmacological activity, for example, as a smooth muscle stimulant action, a hypotensive action, and the like. More specifically, the compounds of the above-described formula wherein R is a pentyl group and $n$ is 6 belong to the groups of prostaglandin-$F_1$. They, therefore, have been of extreme interest in the medical and pharmacological fields.

A few processes for preparing prostaglandins are known, for example, as described in E. J. Corey et al, *J. Am. Chem. Soc.*, 90, 3245–3248 (1968), and in J.E. Pike et al, *J. Am. Chem. Soc.*, 91, 5364–5378 (1969).

SUMMARY OF THE INVENTION

The present inventors have found a novel process for preparing these compounds, which is completely different from these known processes. The process is briefly shown by the following reaction scheme:

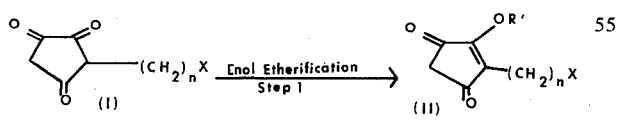

Cyclopentatrione Derivative    Cyclopentatrione – enol Ether Derivative (novel material)

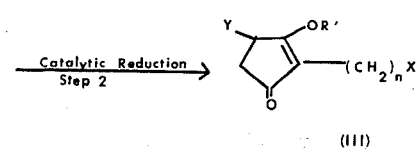

(III)

Cyclopentadione – enol Ether Derivative (novel material)

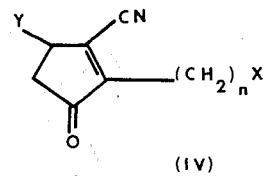

(IV)

3-Cyanocyclopentenone Derivative (novel material)

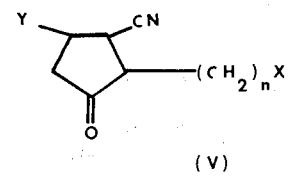

(V)

3-Cyanocyclopentanone Derisvative (novel material)

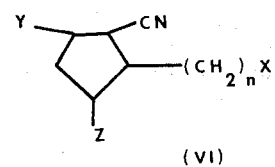

(VI)

3-Cyanocyclopentane-1,4-diol Derivative (novel material)

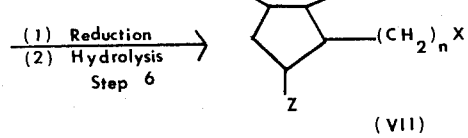

(VII)

3-Formylcyclopentane-1,4-diol Derivative (novel material)

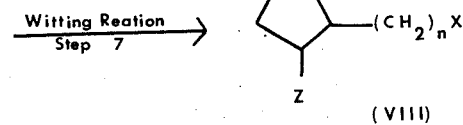

(VIII)

3-$\beta$-Oxoalkenyl-cyclopentane-1,4-diol Derivative

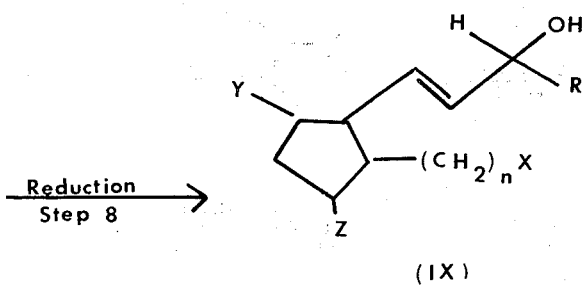

(IX)

Cyclopentane Derivative in the above reaction scheme, R, X, Y, Z and $n$ are as defined above and R' represents a lower alkyl group.

The novelty of the process of this invention includes the steps of producing the novel intermediate products and also the novel reaction of the cyanation of the enol ether [that is, the production of the 3-cyanocyclopentenone derivative (IV) from the cyclopentadione-enol ether derivative (III)].

An object of the present invention is to provide a process for producing a 3-hydroxyalkenylcyclopentane-1,4-diol derivative which is useful as medicines or intermediates for the preparation of other medicines.

Another object of this invention is to provide novel derivatives which are useful as intermediate products for the production of medicines.

Additional objects and advantages of the present invention will be apparent from the following description.

In the present invention, the term homologues of the carboxyl group is a group capable of being readily converted into a carboxyl group or derived from a carboxyl group by a known manner. Examples of such include the $C_1$ to $C_4$ alkoxy-carbonyl group, such as methoxycarbonyl, ethoxycarbonyl and t-butoxycarbonyl or amido groups such as carbamoyl and methylcarbamoyl groups.

As described above, in the present invention Y and Z in the aforesaid formula each represents a hydroxyl group or a homologue of a hydroxyl group. The homologues of a hydroxyl group includes a hydroxyl group protected by a usual protective group. Typical examples of such usual protective groups include etheric protective groups, such as tetrahydropyranyl ether, t-butyl ether, trimethyl silyl ether, benzyl ether, and trityl ether; acrylic protective groups, such as an acetyl group, a benzoyl group, a benzenesulfonyl group, a toluenesulfonyl group, and a benzyloxycarbonyl, group; and a methylidene or a isopropylidene group, when the hydroxyls of Y and Z are in the cis-configuration to each other.

Furthermore, in all of the stages of the present invention, the groups represented by X, Y and Z can take any desired form within the aforesaid scope or definition depending upon the reaction conditions or the after-treatment. For example, when the protective groups for group Y and group Z are tetrahydropyranyl ether groups, the greater part of these protective groups is removed under acidic hydrolysis conditions and the groups protected by such protective groups are converted into hydroxyl.

DETAILED DESCRIPTION OF THE INVENTION

Now, the process of the present invention will be explained by reference to the following stages in due order.

Step 1. Production of a Cyclopentatrione-enol Ether Derivative from a Cyclopentatrione Derivative (I):

The reaction of a cyclopentatrione derivative (I) with an alkylating agent gives a cyclopentatrione-enol ether (II) with a high selectivity with respect to the direction of enol-etherification.

Examples of suitable alkylating agents to be used in this stage, stage 1, include a diazoalkane, such as diazomethane; a lower alcohol, such as methanol, ethanol, and iso-butanol; an alkyl halide, such as methyl iodide, ethyl bromide, and methyl bromide; a dialkyl sulfate, such as dimethyl sulfate and diethyl sulfate; and an ortho-formic acid ester. In case diazomethane is used as the alkylating agent, the enol-etherification can be achieved by mixing an ether solution of diazomethane prepared by a conventional manner and the cyclopentatrione derivative (I).

Further, the reaction can also be carried out, for example, by adding an acid such as sulfuric acid, p-toluenesulfonic acid, and the like, to a solution of the cyclopentatrione derivative (I) in a lower alcohol and heating the mixture obtained. In this case, however, the reaction can be conducted more effectively using an azeotropic dehydration method. Moreover, where an alkyl halide or a dialkyl sulfate is used as the alkylating agent, the reaction is conducted after converting the cyclopentatrione derivative (I) into the sodium salt, the potassium salt, and the like, or is conducted in the presence of a metallic compound, such as sodium hydroxide, potassium hydroxide, sodium amide, sodium methoxide, sodium ethoxide, potassium t-butoxide, sodium sand, and the like.

Furthermore, where an ortho-formic acid ester is used as the alkylating agent, the cyclopentatrione derivative (I) is contacted with the ortho-formic acid ester in the presence of an acidic catalyst, such as sulfuric acid, p-toluenesulfonic acid, boron trifluoride, and the like.

The starting material (I) used in the process of this invention can be obtained by the reaction as shown by the following reaction

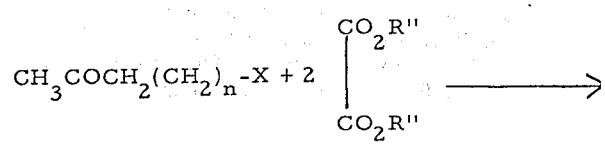

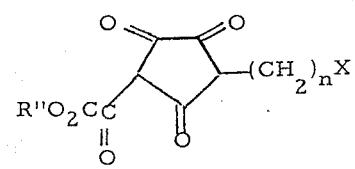

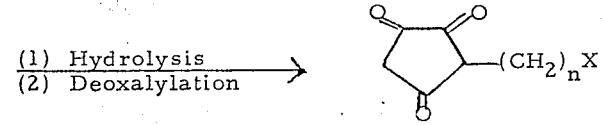

wherein in the reaction formula, X and n are as defined above and R'' represents a lower alkyl group.

Step 2. Production of a Cyclopentadione-enol Ether Derivative (III) from a Cyclopentatrione-enol Ether Derivative (II):

The novel cyclopentatrione-enol ether derivative (II) prepared by Stage 1 is subjected in Step 2 to a catalytic reduction to obtain a novel cyclopentadione-enol ether derivative (III).

The above reaction is achieved by contacting the compound (II) with hydrogen in the presence of a catalyst which is conventionally used in catalytic reductions. Examples of the catalyst include platinum, palladium, nickel, ruthenium, rhodium, and the like, and, from the standpoint of easy preparation of the catalyst and the occurrence of less side reactions, the use of palladium as the catalyst is particularly preferred.

It is preferable to carry out the reaction of this step in the presence of a solvent which is generally employed in catalytic reductions. Suitable solvents are those such as water, methanol, ethanol, propanol, acetic acid, ethyl acetate, benzene and hexane.

The reaction conditions such as hydrogen pressure, reaction temperature and reaction time are conventional catalytic reduction conditions and they are determined by the co-relation of them. The progress of the reaction can be detected by the amount of hydrogen absorbed, and the various reaction conditions can be suitably determined within practical ranges.

For example, when a palladium carbon catalyst is added to the raw material in an amount of from several percent to several tens percent, the reaction proceeds at a satisfactorily practical speed, even under atmospheric pressure and at room temperature.

The novel cyclopentadione-enol ether derivative (III) thus prepared can be purified using, for example, distillation and chromatography, but the reaction product obtained by only filtration and subsequent concentration of the filtrate can be satisfactorily used in the next stage.

The novel cyclopentadione-enol ether derivative (III) thus obtained shows an ultraviolet absorption at 252 mμ in ethanol and by analysis of the nuclear magnetic resonance spectra, it has been confirmed that the direction of the enolation of the compound (III) is as shown by the afore-said chemical formula.

The cyclopentadione-enol ether derivative (III) also can be prepared by subjecting a hydroxy-cyclopentane-1,3-dione represented by the formula

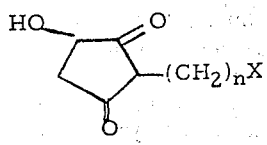

wherein X and n are as defined above, to an enol etherification. However, in this case, beside the desired compound (III), the isomer of this compound represented by the formula

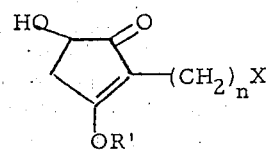

wherein R', X, and n are as defined above, is a by-product and it is quite difficult to separate the by-product from the desired compound (III) due to the similarity in their properties.

Step 3. Production of a 3-Cyanocyclopentenone Derivative (IV) from the Cyclopentadione-enol Ether Derivative (III):

The cyanation of Step 3 in this invention can be achieved by reacting the cyclopentadione-enol ether derivative (III) with cyanide ion or an alkyl-cyanoaluminum.

It is well known that cyanide ion reacts nucleophillically with a simple ketone or an α, β -unsaturated ketone to provide a α -cyanohydrine or a β-cyanoketone, but the cyanation of the cyclopentadione-enol ether derivative of this invention is a novel and unexpected reaction.

The cyanation in the process of this invention can be practiced under various reaction conditions. For example, suitable reaction conditions of using cyanide ion are as follows:

That is, the cyclopentadione-enol ether derivative (III) can be contacted with hydrocyanic acid in an inert solvent in the presence of a basic catalyst, the derivative (III) can be contacted with a metal salt of hydrocyanic acid, derivative (III) can be contacted with a metal salt of hydrocyanic acid in the presence of a catalyst, derivative (III) can be contacted with a metal salt of hydrocyanic acid together with an ammonium salt of a strong acid, derivative (III) and acetone cyanohydrine can be contacted in the presence of a basic catalyst, and derivative (III) can be contacted with hydrocyanic acid activated by trialkylaluminum.

The reaction modes can be varied depending upon the reaction method employed but they are the same from the standpoint that cyanide ion or activated cyanide ion is caused to react nucleophillically with the compound (III).

On the other hand, the reaction can be also carried out using an alkylcyanoaluminum. In this case, the reaction modes are as follows:

The compound (III) is caused to react with the alkyl-cyanoaluminum in the presense or absence of an inert solvent. In practice, the reaction proceeds even under extremely mild conditions, for example, the reaction is completed in a short period of time at a reaction temperature of about room temperature. Examples of the inert solvent to be employed in the reaction include tetrahydrofuran, ethanol, isopropanol, benzene, toluene, hexane, heptane, methylene chloride, and the like. The alkylcyanoaluminum used in this invention can also be represented by the following formula $$Al(CN)_2R_{2-m}{}^{IV}R_m{}^V$$

wherein $R^{IV}$ represents an alkyl group, RV represents an alkoxy group or a halogen, and m is 0 or 1. Typical examples are dimethylaluminum cyanide, diethylaluminum cyanide, dipropylaluminum cyanide, diisobutylaluminum cyanide, ethylaluminum chloride cyanide, and the like. These compounds can be prepared by known methods.

The novel 3-cyanocyclopentenone derivative (IV) prepared in this step of this invention is a viscous liquid and shows the specific infrared absorption spectra of a nitrile group and an unsaturated ketone group. Also, the material shows a maximum absorption band in the ultraviolet absorption spectra at about 240 m$\mu$.

Step 4. Production of a 3-Cyanocyclopentanone Derivative (V) from the 3-Cyanopentenone Derivative (IV):

In this step, the 3-cyanocyclopentenone derivative (IV) is brought into contact with zinc in the presence of an acidic solvent, whereby the carbon-carbon double bond is selectively reduced and a 3-cyanocyclopentanone derivative (V) is obtained.

Examples of acidic solvents include organic acids, such as acetic acid, formic acid and propionic acid; inorganic acids, such as hydrochloric acid, sulfuric acid, and the like; and the mixtures thereof. In addition, an inert solvent such as an alcohol, benzene, an ether, and hexane can be used, if desired.

The reaction temperature and the reaction period of time can be properly selected but in general it is preferable to conduct the reaction under mild conditions. For example, in the mixed solvent system of acetic acid and hydrochloric acid, the reaction proceeds satisfactorily even under ice-cooling.

Since the 3-cyanoyclopentanone derivative (V) has three asymmetric carbon atoms, it is theoretically possible that four diastereomers are present. But by the steric selectivity of the reaction, the relative configuration of the substituent at the 2-position and the cyano group at the 3-position appears to be the trans form. Therefore, the diastereoisomerism of the compound mainly depends on the steric configuration of the hydroxyl or its homologue at the 4-position. These isomers can be separated from each other, if desired, by means of, for example, chromatography. The novel 3-cyanocyclopentanone derivative (V) prepared in step 4 of the process of this invention is generally obtained as an oily material.

The 3-cyanocyclopentanone derivative (V) has no ultraviolet absorption at 240 m$\mu$($\lambda$ max EtOH) which is observed in the material (IV) and this phenomenon can be utilized as a method of controlling the reaction.

Step 5. Production of a 3-Cyanocyclopentane-1,4-diol Derivative (IV) from the 3-Cyanocyclopentanone Derivative (V):

The 3-cyanocyclopentanone derivative (V) is converted into a 3-cyanocyclopentane-1,4-diol derivative (VI) by reduction with a metal borohydride or a metal tri-t-butoxyaluminum hydride in this stage. Examples of metal borohydrides include various alkali metal borohydrides and alkaline earth metal borohydrides, such as sodium borohydride, potassium borohydride, lithium borohydride, zinc borohydride, magnesium borohydride, calcium borohydride, and the like. Sodium borohydride and potassium borohydride are preferred, because they affect strongly ketone groups but not carboxyl groups or their homologues and cyano groups. Examples of the metal tri-t-butoxyaluminum hydrides include lithium tri-t-butoxyaluminum hydride, sodium tri-t-butoxyaluminum hydride, and the like.

In the reduction of this step it is preferable to employ an inert solvent. Examples of suitable solvents include, in the case of the reduction by a metal borohydride, water; alcohols, such as methanol, ethanol, isopropanol, and the like; and ethers, such as tetrahydrofuran, dioxane, ethyl ether, dimethoxyethane, and the like, and in the case of the reduction by metal tri-t-butoxyaluminum hydride, ethers such as tetrahydrofuran, ethyl ether, dioxane, dimethoxyethane, and the like.

The reducing agents can be used in a stoichiometrically equal or greater amount.

Especially, reducing agents such as sodium borohydride, potassium borohydride, lithium tri-t-butoxyaluminum hydride can be used in a large excess without any detrimental effects because of their reaction selectivity.

Step 6. Production of a 3-Formylcyclopentane-1,4-diol Derivative (VII) from the 3-Cyanocyclopentane-1,4-diol Derivative (VI):

The 3-cyanocyclopentane-1,4-diol derivative (VI) is partially reduced to an aldimine on treatment with stannous chloride and hydrogen chloride or on treatment with lithium aluminum hydride, sodium aluminum hydride or the metal aluminum hydride compound in which from 1 to 3 hydrogen atoms thereof have been substituted with lower alkoxy groups and further the aldimine is hydrolyzed into an aldehyde.

The partial reduction of the cyano group with stannous chloride and hydrogen chloride is generally called, including a hydrolysis which will inevitably occur in the subsequent step, the Stephen reaction and various reaction conditions can be employed. That is, in the reaction of this stage, it can be fundamentally achieved by subjecting the 3-cyanocyclopentane-1,4-diol derivative (VI) to contact with stannous chloride and hydrogen chloride in an invert solvent. Examples of the preferred inert solvents include ethers, such as diethyl ether, diisopropyl ether, dioxane, and the like. In this reaction, stannous chloride can be used in a great molar excess to an amount equal to the amount of the 3-cyanocyclopentane-1,4-diol derivative (VI) and also hydrogen chloride is usually used in an excess amount. Furthermore, the reaction temperature can be suitably selected in the temperature range lower than the boiling temperature of the solvent to be used.

The aldimine formed by the reaction of this step is a complex salt with stannous chloride and hydrochloride, and since the complex salt is in a syrupy or powdered state it can be isolated readily from the reaction system.

When the complex salt-type aldimine thus isolated or the crude reaction product mixture is brought into contact with water, the aldimine is hydrolyzed to provide the desired 3-formylcyclopentane-1,4-diol derivative (VII), which can be isolated from the reaction system using extraction, and the like.

Preferred examples of the metal aluminum hydride compounds used in the reaction in the other embodiment of this step of the invention are trialkoxy compounds such as lithium triethoxyaluminum hydride and the like. The reaction by such metal aluminum hydride compounds is achieved in a conventional manner, that is, by mixing and reacting the cyano compound (VI) and the metal aluminum hydride compound in an inert solvent. Examples of preferred inert solvents in this case are diethyl ether, tetrahydrofuran, and dioxane and the like. On the other hand, the amount of the metal aluminum hydride compound used in the reaction is desirably a stoichiometric amount to the amount of the cyano compound (VI) to be employed or approximately a stoichiometric amount.

By ordinary hydrolysis of the aldimine thus obtained, the desired aldehyde compound (VII) can be obtained.

The aldehyde compound (VII) thus obtained can be supplied to the subsequent step as is or can be purified by means of conventional techniques such as chromatography.

Step 7. Production of a 3-γ-Oxoalkenylcyclopentane-1,4-diol Derivative (VIII) from the 3-Formylcyclopentane-1,4-diol Derivative (VII):

The 3-γ-oxoalkenylcyclopentane-1,4-diol derivative (VIII) is obtained by reacting the 3-formylcyclopentane-1,4-diol derivative (VII) with a so-called Wittig reagent represented by the formula

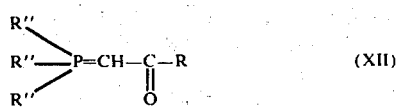

(XII)

wherein R is as defined above and R'' represents an alkyl or an aryl group, or a modified Wittig reagent represented by the formula

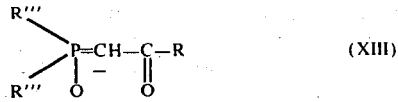

(XIII)

wherein R is as defined above and R''' represents an aryl group or an alkoxy group.

The reaction can be practiced in various modes, for example, the reaction can be carried out by directly heating the mixture of the starting substances or by heating them in an inert solvent such as diethyl ether, tetrahydrofuran, dioxane, benzene, toluene, xylene, methanol, ethanol, methylene chloride, dimethyl formamide, dialkoxyethane, and the like. The reaction temperature can be suitably selected, and the reaction can proceed even at temperatures lower than room temperature but the reaction rate can be accelerated by heating. Furthermore, the ratio of the amount of the 3-formylcyclopentane-1,4-diol derivative (VII) to that of the Wittig reagent (XII) or the modified Wittig reagent (XIII) can be appropriately selected. Generally, it is preferable to carry out the reaction in an equimolar ratio or the like.

The desired 3-oxoalkenylcyclopentane-1,4 -diol derivative (VIII) can be obtained generally as an oily material and can be isolated and purified using conventional techniques such as chromatography.

The Wittig reagent or the modified Wittig reagent to be used in the process of this invention can be prepared in a known method. Examples of the Wittig reagent (XII) include formylmethylene triphenylphosphorane, acetylmethylene triphenylphosphorane, butanoylmethylene triamylphosphorane, hexanoylmethylene tritolylphosphorane, hexanoylmethylene tributylphosphorane, and the like.

On the other hand, the modified Wittig reagent (XIII) is shown as an anion-type reagent and is prepared by treating a dialkylacylmethyl phosphonate or a diarylacylmethyl phosphine oxide with a base such as phenyl lithium, butyl lithium, or sodium hydride to form the metal salt thereof.

Step 8. Production of a 3-Hydroxyalkenylcyclopentane Derivative (IX) from the 3-Oxoalkenylcyclopentane-1,4-diol Derivative (VIII):

The 3-oxoalkenylcyclopentane-1,4-diol derivative (VIII) obtained in step 7 is reacted with a metal borohydride or a metal tri-t-butoxyaluminum hydride in an inert solvent in order to obtain the desired 3-hydroxyalkenylcyclopentane derivative (IX). The reaction of this step can be carried out using various reaction conditions within conventional reduction conditions. Examples of metal borohydrides include alkali metal borohydrides, such as sodium borohydride, potassium borohydride, lithium borohydride, and the like, alkaline earth metal borohydrides, such as magnesium borohydride, calcium borohydride, and the like. Use of sodium borohydride and potassium borohydride gives good results because they affect strongly conjugated carbonyls but hardly affect other functional groups of the 3-oxoalkenylcyclopentane-1,4-diol derivative (VIII).

On the other hand, examples of metal tri-t-butoxyaluminum hydrides include lithium tri-t-butoxyaluminum hydride, sodium tri-t-butoxyaluminum hydride, and the like.

Examples of the inert solvent include, in the case of the reduction using a metal borohydride, water, alcohols such as methanol, ethanol, isopropanol, and the like, and ethers such as diethyl ether, tetrahydrofuran, dioxane, dimethoxyethane, and the like, and in the case of the reduction using a metal tri-t-butoxyaluminum hydride, include ethers such as diethyl ether, tetrahydrofuran, dioxane, dimethoxyethane, and the like.

Reaction conditions of temperature and period of time can be varied within conventional reduction conditions.

Although the cyclopentane derivatives (IX) include various stereoisomers, the process of the present invention can be applied to the production of all the stereoisomers, and it is possible to produce the desired cyclopentane derivative (IX) in the form of a desired and specified stereoisomer or a mixture of various stereoisomers.

The invention will now be explained in greater detail by reference to the following examples without limiting the invention thereby.

EXAMPLE 1

Production of 1-(3'-Hydroxy-1'-octenyl)-2-(6'-carbomethyoxyhexyl)-3,5-dihydroxy-cyclopentane:

(R = -n-C$_5$H$_{11}$; X = —COOCH$_3$; Y and Z = —OH; n = 6):

Step 1

Thirty grams (30 g) of 2-(6'-carboxyhexyl)cyclopentan-1,3,4-trione having a melting point of 103°C was treated with an ether solution of an excess amount of diazomethane in a conventional manner. The reaction product obtained was subjected to conventional after-treatment and distillation to give 25 g of 2-(6'-carbomethoxyhexyl)-3-methoxy-4-oxo-2-cyclopenten-1-one, b.p. 165°C/0.4–0.6 mmHg, n$_D^{24.5}$ 1.4992.

Step 2

An isopropanolic solution (190 ml) of 24 g of 2-(6'-carbomethoxyhexyl)-3-methoxy-4-oxo-2-cyclopenten-1-one prepared in Step 1 and 2.85 g. of a 5% palladium carbon catalyst was subjected to catalytic hydrogenation under atmospheric pressure at room temperature until 2.3 liter of hydrogen gas was absorbed. The reaction mixture was treated according to a conventional method to give the desired compound, 2-(6'-carbomethoxyhexyl)-3-methoxy-4-hydroxy-2-cyclo-penten-1-one.

In the nuclear magnetic resonance spectra of the product, a singlet signal due to the methyl ester proton appeared at 3.65 ppm.

Step 3

(a):

A toluene solution of diethylaluminum cyanide was prepared by reacting 15.7 g of triethylaluminum with 4.1 g of hydrocyanic acid in 300 ml of toluene. Into the obtained toluene solution of diethylaluminium cyanide was added a mixture of 15.4 g of 2-(6'-carbomethoxyhexyl)-3-methoxy-4-hydroxy-2-cyclopenten-1-one prepared in Step 2 under cooling and the resultant mixture was allowed to stand for 2 hours at room temperature. The reaction mixture was poured into diluted hydrochloric acid under cooling. The organic layer thus formed was separated, and the aqueous layer was extracted with ether. The combined organic layers were washed with aqueous sodium bicarbonate solution and then water and dried over magnesium sulfate. After evaporation of the solvent, the residual oil was purified using chromatography on silica gel to provide 11.6 g of 2-(6'-carbomethoxyhexyl)-3-cyano-4-hydroxy-2-cyclopenten-1-one as an oily material.

(b):

A mixture of 1.75 g of 2-(6'-carbomethoxyhexyl)-3-methoxy-4-hydroxy-2-cyclopenten-1-one, 0.97 g of potassium cyanide, and 0.65 g of ammonium chloride was refluxed for 2.3 hours in a mixture of 1.46 g of water and 14.5 g of tetrahydrofuran with stirring.

After the reaction was over, the liquid portion was separated from the crystalline precipitate by decantation. After the reaction liquid separated was acidified by dropwise addition of hydrochloric acid, the greater part of the tetrahydrofuran was distilled off under reduced pressure and the residual oil was dissolved in ether. The ether layer was washed with water and then aqueous sodium bicarbonate solution and dried over magnesium sulfate. When the ether was distilled off and the oily product thus obtained was purified by chromatography on silica gel, 0.25 g of 2-(6'-carbomethoxyhexyl)-3-cyano-4-hydroxy-2-cyclopenten-1-one was obtained as an oily substance.

Infrared absorption spectrum (film, unit, $cm^{-1}$): 3450, 3225, 1725, 1630, 1440, 1255, 1200 and 1170.

Also, when a nuclear magnetic resonance spectrum * (60 Mc) of the above compound were measured, the three protons of the 5-membered rings showed specific signals. That is, the proton at the 4-position and the two types of protons at the 5-position show ABX-type signals analyzed approximately first order. Their chemical shifts and coupling constant (J) were as follows: the proton at the 4-position (5.05, multiplet), the proton at the 5-position at the same side as the proton at the 4-position (2,9, double doublet, J = 6 cps, 19 cps), and the proton at the 5-position opposite to the proton at the 4-position (2.45, double doublet, J = 2.5 cps, 19 cps).

* All of the nuclear magnetic resonance spectra were obtained using a Varian-T-60, and they were taken in $CDCl_3$.

The chemical shifts are given in value, as ppm ($\delta$) with respect to tetramethylsilane.

Step 4

Into a mixture of 7 g of 2-(6'-carbomethoxyhexyl)-3-cyano-4-hydroxy-2-cyclopenten-1-one, 52.5 ml of acetic acid and 55 ml of 0.5 N hydrochloric acid was added 15 g of zinc powder. After the addition the reaction mixture was stirred for 3 hours under cooling. Thereafter, the zinc powder was removed by filtration, and the filtrate was diluted with water and extracted with ether. The ether extract was washed with a diluted aqueous sodium bicarbonate solution and with water and then dried. The solvent was distilled off to afford 4.5 g of 2-(6'-carbomethoxyhexyl)-3-cyano-4-hydroxy-cyclopentanone.

Infrared absorption spectrum ($cm^{-1}$): 3450, 2250, 1740, 1265, 1240, 1205 and 1170.

Nuclear magnetic resonance spectrum: about 4.8 (H, multiplet, carbinol methine type proton), 3.6 (3H, singlet methyl ester type protons), wherein H represents a number of hydrogens.

Step 5

Into a suspension of 8 g of lithium tri-t-butoxyaluminum hydride in 90 ml of absolute tetrahydrofuran was added dropwise 4.0 g of 2-(6'-carbomethoxyhexyl)-3-cyano-4-hydroxy-cyclopentanone under ice-cooling. The obtained mixture remained under ice-cooling for 1.5 hours and then at room temperature for 0.5 hours. After cooling, acetone and an aqueous solution saturated with ammonium sulfate were added to the reaction mixture to decompose the excess lithium tri-t-butoxyaluminum hydride and the complex salt product. The resultant oily layer was extracted with ethyl acetate, and the extract was washed with water, dried and then concentrated to afford 3.2 g of 2-(6'-carbomethoxyhexyl)-3-cyano-cyclopentane-1,4-diol as an oily substance, which was purified using chromatography on silica gel.

Infrared absorption spectrum (unit: $cm^{-1}$): 3420, 2225, 1730, 1710, 1240, 1170, 1085 and 1020.

Nuclear magnetic resonance spectrum: about 4.0 (H, multiplet, carbinol methine type proton at the 1-position), about 4.5 (H, multiplet, carbinol methine type proton at the 4-position). 3.65 (3H, singlet, methyl ester type protons).

The cyano-cyclopentane-diol derivative thus obtained was contacted with acetic anhydride to yield the corresponding diacetate as an oily substance.

Infrared absorption spectrum (unit: $cm^{-1}$): 2230, 1735, 1360, 1220, 1175 and 1030.

Nuclear magnetic resonance spectrum: about 4.9 (H, multiplet, methine type proton at the 1-position), about 5.3 (H, multiplet, methine type proton at the 4-position), 3.65 (3H, singlet, methyl ester type protons) and about 2.0 (6H, singlet, acetoxymethyl type protons).

| Elementary Analysis | C (%) | H (%) | N (%) |
| --- | --- | --- | --- |
| Calculated (for $C_{18}H_{27}O_6N$) | 61.17 | 7.70 | 3.96 |
| Found | 61.56 | 7.68 | 3.69 |

Step 6

(a):

Into a solution of 100 ml of absolute ether and 1.4 g of 2-(6'-carbomethoxyhexyl)-3-cyano-1,4-diacetoxy-cyclopentane was introduced a hydrogen chloride gas under ice-cooling until saturated with hydrogen chloride. Further, while continuing the introduction of the hydrogen chloride gas, 1.4 g of anhydrous stannous chloride was added to the solution 6 times every 20 minutes under ice-cooling. After further continuing the reaction for 6 hours at room temperature, the reaction mixture was concentrated under reduced pressure to provide a syrupy material. The material was treated with absolute ether to deposit a yellow powdery material which was recovered by filtration and brought into contact with a cooled aqueous sodium chloride solution by shaking to conduct the hydrolysis of the product. The ether layer was washed with an aqueous sodium bicarbonate solution and then aqueous sodium chloride solution, and dried over magnesium sulfate. Ether was distilled off to provide 0.5 g. of 2-(6'-carbomethoxyhexyl)-3,5-diacetoxy-cyclopentane carboaldehyde.

Infrared absorption spectrum (unit: $cm^{-1}$): 2825, 2750, 1735, 1720, 1250, 1240, 1175, 1100 and 1030.

Nuclear magnetic resonance spectrum: 9.85 (H, doublet, J = 2 cps, aldehyde type proton), about 5.4 (H, multiplet, methine type proton at the 5-position), about 5.0 (H, multiplet, methine type proton at the 3-position) and 3.65 (3H, singlet, methyl ester type protons).

(b):

Into a mixture of 500 mg of lithium triethoxyaluminum hydride in 10 ml of absolute ether was added dropwise 20 ml of a solution of 540 mg of 2-(6'-carbomethoxyhexyl)-3-cyano-1,4-diacetoxy-cyclopentane in absolute ether. After the reaction mixture was stirred for 1 hour at room temperataure, the mixture was treated with 25 ml of 3N-sulfuric acid under ice-cooling for hydrolysis. When the product was extracted with ether and then treated according to a conventional manner, about 400 mg of a crude product oil was obtained. By the analysis of the infrared absorption spectra and the nuclear magnetic resonance spectra, the formation of 2-(6'-carbomethoxyhexyl)-3,5-diacetoxy-cyclopentane carboaldehyde was confirmed.

Step 7

A mixture of 200 ml of absolute ether, 470 mg of 2-(6'-carbomethoxyhexyl)-3,5-diacetoxy-cyclopentane carboaldehyde and 450 mg of hexanoylmethylene tributylphosphorane was stirred for 48 hours at room temperature. Thereafter, the reaction mixture was concentrated and the resultant residue was purified using chromatography on silica gel, whereby 350 mg of liquid 1-(3'-oxo-1'-octenyl)-2-(6'-carbomethoxyhexyl)-3,5-diacetoxy-cyclopentane was obtained.

| Elementary Analysis | C (%) | H (%) |
|---|---|---|
| Calculated (for $C_{25}H_{40}O_7$) | 66.34 | 8.87 |
| Found | 66.34 | 8.91 |

Infrared absorption spectrum (film, unit, $cm^{-1}$): 1735, 1695, 1675, 1630, 1370, 1230, 1180 and 1030.

Nuclear magnetic resonance spectrum:

The enolic unsaturated protons appeared as a doublet (J = 16 cps) and a double doublet (J = 16 cps, J = 8 cps), at 6.1 and 6.7, respectively.

Also, the signal of the methyl proton of the acetate appeared as singlets at about 2.0 and the signal of the methine protons at the 3 and the 5 position appeared as a multiplet at about 5.0. Further, the signal of the methyl proton of the methyl ester appeared as a singlet as 3.6 and also the signal of the terminal methyl protons of the octenyl appeared as a triplet (J = 7 cps) at 0.9.

Ultraviolet absorption spectrum ($\lambda_{max}$EtOH): 225 mµ.

Step 8

Into a mixture of 123 mg of 1-(3'-oxo-1'-octenyl)-2-(6'carbomethoxyhexyl)-3,5-diacetoxy-cyclopentane and 30 ml of methanol was added dropwise a mixture of 350 mg of sodium borohydride in 35 ml of methanol under ice-cooling. After the addition, the reaction mixture was stirred for 45 minutes a mixture of 350 mg of sodium borohydride in 35 ml of methanol was added dropwise again, and the stirring was continued for 45 minutes. The reaction mixture was stirred for additional 45 minutes at room temperature. After cooling, acetone was added to decompose the excess of sodium borohydride. The obtained mixture was concentrated under a reduced pressure to yield an oily substance, which was decomposed by the addition of a cold aqueous ammonium chloride solution. The organic layer was extracted with ethyl acetate and treated in a conventional manner to give 100 mg of an oily substance consisting of 1-(3'-hydroxy-1'-octenyl)- 2-(6'-carbomethoxyhexyl)-3,5-diacetoxy-cyclopentane and a partly deacetylated compound. The oily substance obtained thus was saponified by reaction with 1 g of a 10%-aqueous NaOH solution in the presence of 1 g of methanol under cooling. After the saponification, the reaction mixture was acidified, and the separated acidic substance was extracted with ethyl acetate and then treated according to a conventional manner to yield 93 mg of semi-solid of 1-(3'-hydroxy-1'-octenyl)-2-(6'-carboxyhexyl)-cyclopenane-3,5-diol ("Prostagrandin-$F_1$").

Infrared absorption spectrum (unit: $cm^{-1}$): 3775, 3000-2600, 1710, 1265, 1100, 1050 and 970.

Subsequently 1-(3'-hydroxy-1'-octenyl)-2-(6'-carboxyhexyl)-cyclopentane-3,5-diol was converted into the corresponding methyl ester on treatment with diazomethane and then purified using chromatography on silica gel to give a semisolid of 1-(3'-hydroxy-1'-octenyl)3-(6'-carbomethoxyhexyl)-cyclopentane-3,5-diol.

Infrared absorption spectrum ($CHCL_3$ solution, $cm^{-1}$): 3450, 1730, 1260, 1090, 1030, and 970.

Nuclear magnetic resonance spectrum: about 5.6 (2H, multiplet, unsaturated protons at the 1'-position and the 2'-position), about 4.0 (3H, multiplet, three carbinol type methine protons), 3.7 (3H, singlet, methyl ester type protons), 0.9 (3H, triplet, terminal methyl type protons at the 8'-position).

Mass spectrum: 352 (M-18), 334 (M-36). 280 (M-18-72). M+ was not observed because of its weak signal.

| Elementary Analysis | C (%) | H (%) |
|---|---|---|
| Calculated (for $C_{21}H_{38}O_5$) | 68.07 | 10.34 |

| Elementary Analysis | C (%) | H (%) |
|---|---|---|
| Found | 68.12 | 10.25 |

EXAMPLE 2

Production of 1-(3'-Hydroxy-1'-octenyl)-2-(6'-carboethoxyhexyl)-3,5-diacetoxy-cyclopentane:

(R = -n-$C_5H_{11}$; X = —$COOC_2H_5$; Y and Z = —O—$COCH_3$; n = 6)

Step 1

Five grams (5 g) of 2-(6'-carboethoxyhexyl)-cyclopentan-1,3,4-trione was reacted with diazomethane in ether according to conventional procedures to give 3.8 g of 2-(6'-carbethoxyhexyl)-3-methoxy-4-oxo-2-cyclopenten-1-one, b.p. 165°–170°C/0.4–0.6 mmHg.

Infrared absorption spectrum (film, unit, cm$^{-1}$): 1735, 1695, 1620, 1350, 1190, and 1150.

Nuclear magnetic resonance spectrum: 4.28 (3H, singlet, methyl enol ether type protons), 2.88 (2H, singlet, methylene type protons at the 5-position).

Step 2

The procedure similar to that of Step 2 of Example 1 was repeated except that 2.82 g of 2-(6'-carbethoxyhexyl)-3-methoxy-4-oxo-2-cyclopenten-1-one and 35 ml of methanol were used instead of 24 g of 2-(6'-carbomethoxyhexyl)-3-methoxy-4-oxo-2-cyclopenten-1-one and isopropanol respectively to provide 2.8 g of 2-(6'-carboethoxyhexyl)-3-methoxy-4-hydroxy-2-cyclopenten-1-one as an oily product.

The compound thus prepared had the following properties:

Infrared absorption spectrum (film, unit, cm$^{-1}$): 3400, 1735, 1700 (shoulder), 1625, 1365, 1260, 1170 and 1050.

Nuclear magnetic resonance spectrum (unit: cm$^{-1}$): 4.95 (H, double doublet, J = 6 cps and 1.8 cps), 4.13 (3H, singlet), 4.12 (2H, quartet, J = 7 cps), 2.78 (H, double doublet, J = 18 cps and 6 cps), 2.32 (H, double doublet, J = 18 cps and 1.8 cps) and 1.25 (3H, triplet, J = 7 cps).

A part of the compound thus prepared could be converted into the 4-acetyl compound using conventional methods.

Step 3

(a):

The procedure similar to that of Step 3 (a) of Example 1 was repeated using 9.4 g of 2-(6'-carbethoxyhexyl)-3-methoxy-4-hydroxy-2-cyclopenten-1-one, 8.2 g of triethyl aluminum, 2.0 g of hydrocyanic acid, and a mixed solvent of benzene and toluene to provide 4.1 g of oily 2-(6'-carbethoxyhexyl)-3-cyano-4-hydroxy-2-cyclopenten-1-one.

The properties of the compound thus obtained were as follows:

Infrared absorption spectrum (film, unit, cm$^{-1}$): 3450, 2225, 1725, 1630, 1440, 1235 and 1170.

Also, when the nuclear magnetic resonance spectrum of the compound was measured, the three protons of the five-membered ring showed specific signals. That is, the proton at the 4-position and the two protons at the 5-position showed ABX-type analyzed at approximately first order. The chemical shift and coupling constant, and J were as follows:

Proton at the 4-position: 5.05, multiplet; proton at the 5-position at the same side as the proton of the 4-position; 2.9, double doublet, J = 6 cps and 19 cps; and the proton at the 5-position opposite to the 4-position proton: 2.45, double doublet, J = 2.5 cps and 19 cps.

(b):

According to the procedure similar to that of Step 3 (a) of Example 1, 0.52 g of 2-(6'-carbethoxyhexyl)-3-methoxy-4-acetoxy-2-cyclopenten-1-one prepared in Step 2 was caused to react with diethylaluminum cyanide. Further, the product was purified using chromatography on silica gel to provide 0.25 g of 2-(6'-carbethoxyhexyl)-3-cyano-4-acetoxy-2-cyclopenten-1-one as an oily material.

The properties of the product were as follows:

Infrared absorption spectrum (film, cm$^{-1}$): 2239, 1755–1730, 1370, 1240, 1175 and 1045.

Step 4

Into a mixture of 8 ml of acetic acid and 5 ml of 0.1 N hydrochloric acid was dissolved 1.2 g of 2-(6'-carbethoxyhexyl)-3-cyano-4-hydroxy-2-cyclopenten-1-one and under ice-cooling the mixture was stirred for 4 hours with the addition of 4 g of zinc powder. The zinc powder in the reaction mixture was filtered off, and after diluting the filtrate with 50 ml of water, the product was extracted with ether and then ethyl acetate. The combined organic layers were washed with aqueous sodium bicarbonate solution and then water and dried.

After evaporation of the solvents, the residue was purified using chromatography on silica gel to provide 0.50 g of 2-(6'-carbethoxyhexyl)-3-cyano-4-hydroxy-cyclopentanone.

The product thus obtained was an oily material and had the following properties:

Infrared absorption spectrum (film, unit: cm$^{-1}$): 3450, 2250, 1740 (broad), 1240 and 1180.

| Elementary Analysis | C (%) | H (%) | N (%) |
|---|---|---|---|
| Calculated (for $C_{15}H_{23}O_4N$) | 64.03 | 8.24 | 4.98 |
| Found | 63.89 | 8.04 | 4.61 |

Step 5

Into an ethanolic solution (38 ml) of 1.26 g of 2-(6'-carbethoxyhexyl)-3-cyano-4-hydroxy-cyclopentanone was added 0.4 g of sodium borohydride under ice-cooling, followed by stirring for 2 hours with continuing ice-cooling. To the reaction mixture was added 15 ml of acetone to decompose the excess sodium borohydride. Evaporation of the solvent under reduced pressure provided a syrupy residue, which was decomposed by an aqueous ammonium chloride solution.

The resultant organic layer was extracted with ethyl acetate, and the extract was worked up in a usual manner to give 1.06 g of 1-(6'-carbethoxyhexyl)-3-cyano-cyclopentane-1,4-diol.

The properties of the compound thus obtained were as follows:

Infrared absorption spectrum (unit: cm⁻¹): 3420, 2225, 1730, 1710, 1240, 1170, 1085 and 1020.

Nuclear magnetic resonance spectrum: 4.15 (2H, quartet, ester methylene protons).

The product was converted into the corresponding 1,4-diacetate and 1,4-ditetrahydropyranyloxy derivative in a conventional manner.

Step 6

(a):
The procedure similar to that in Step 6 (a) of Example 1 was repeated using 800 mg of 2-(6'-carbethoxyhexyl)-3-cyano-1,4-diacetoxy-cyclopentane, 800 mg of anhydrous stannous chloride, and 50 ml of absolute ether to provide a crude oily product containing 2-(6'-carbethoxyhexyl)-3,5-diacetoxy-cyclopentane carboaldehyde. The product was purified using chromatography. Yield: 275 mg.

(b):
The procedure similar to that in Step 6(a) of Example 1 was repeated using 350 mg of 2(6'-carbethoxyhexyl)-cyano-1,4-ditetrahydropyranyloxy-cyclopentane, 250 mg of anhydrous stannous chloride, and 30 ml of absolute ether to provide 250 mg of a crude oily product. By analysis of the infrared absorption spectra and the nuclear magnetic resonance spectra, it is confirmed that the product contained the desired carboaldehyde derivative. Also, by subjecting a part of the product to thin-layer chromatography, the desired 2-(6'-carboethoxyhexyl)-3,5-dihydroxycyclopentane carboaldehyde was detected by a spot showing a low $R_f$ value.

Step 7

(a):
A mixture of 250 mg of 2-(6'-carboethoxyhexyl)-3,5-diacetoxycyclopentane carboaldehyde and 200 mg of sodium salt-type diethylhexanoylmethyl phosphonate in dimethoxy ethane was stirred for 48 hours at room temperature, the reaction liquid was poured into cold diluted hydrochloric acid. The resultant oily product was extracted with ether and the ethereal extract was post-treated in a conventional manner to provide 200 mg of oily 1-(3'-oxo-1'-octenyl)-2-(6'-carbethoxyhyexyl)-3,5-diacetoxycyclopentane.

The nuclear magnetic resonance spectrum of the compound was almost same as those of the carbomethoxy compound obtained in Step 7 of Example 1 except that the methylene proton signal of the ethyl ester appeared as a quartet (J = 7 cps) at 4.1.

Step 8

Into a suspenson of 1.0 g of lithium tri-t-butoxyaluminum hydride in 8 ml of absolute tetrahydrofuran was added dropwise 200 mg of 1-(3'-oxo-1'-octenyl)-2-(6'carbethoxyhexyl)-3,5-diacetoxy-cyclopentane under ice-cooling. The resultant mixture was stirred for 1.5 hours under ice-cooling and then for 1 hour at room temperature. After cooling, acetone and an aqueous solution saturated with ammonium sulfate were added to the reaction mixture to decompose the excess lithium tri-t-butoxyaluminum hydride and the complex salt product.

The resultant oily layer was extracted with ethyl acetate, and the extract was washed with water, dried and then concentrated to afford 120 mg of 1-(3'-hydroxy-1'-octenyl)-2-(6'-carbethoxyhexyl)-3,5-diacetoxycyclopentane. The properties of this compound were as follows:

In its nuclear magnetic resonance spectrum, the signal due to the olefinic protons appeared at about 5.6 as a multiplet. The signal due to the methine protons at the 3- and the 5-position appeared at about 5.0 as a mutliplet. Moreover, specific signals at about 2.0 (singlet, acetoxy methyl protons) and 4.15 (quartet, ester methylene protons) were observed.

EXAMPLE 3

Production of
1-(3'-Hydroxy-1'-propenyl)-2-(6'-carbethoxyhexyl)-3,5-diacetoxy-cyclopentane (R = H; X = —COOC₂H₅; Y = Z = —O—COCH₃; n = 6):

Steps 1–6

According to the procedures similar to those in Steps 1–6 of Example 2, 2-(6'-carbethoxyhexyl)-3,5-diacetoxy-cyclopentane carboaldehyde was obtained.

Step 7

A mixture of 10 ml of chloroform, 200 mg of 2-(6'-carbethoxyhexyl)-3,5-diacetoxy-cyclopentane carboaldehyde and 500 mg of formylmethylene triphenyl phosphorane was stirred for 5 days at room temperature. When the reaction product was purified using chromatography on silica gel, about 50 mg of 1-(3'-oxo-1'-propenyl)-2-(6'-carbethoxyhexyl)-3,5-diacetoxy-cyclopentane was obtained.

In the nuclear magnetic resonance spectrum of the compound, the aldehyde proton appeared as a doublet (J = 8 cps) at about 9.5.

Step 8

Into an ethanolic solution (10 ml) of 80 mg of 1-(3'-oxo-1'-propenyl)-2-(6'-carbethoxyhexyl)-3,5-diacetoxy-cyclopentane was added 200 mg of sodium borohydride under ice-cooling, followed by stirring for an additional hour with continuing ice-cooling.

The mixture obtained was worked up by a usual manner to give an oily material containing the objective 1-(3'-hydroxy-1'-propenyl)-2-(6'-carbethoxyhexyl)-3,5-diacetoxy-cyclopentane.

In its nuclear magnetic resonance spectrum, the signal due to the olefinic protons of the propenyl chain was observed at about 5.5 as a multiplet.

What is claimed is:
1. A 3-cyanocyclopentenone derivative having the formula

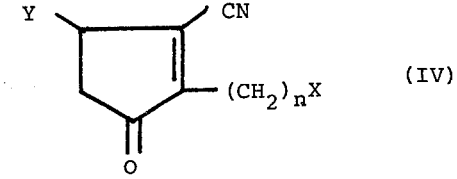

(IV)

wherein X is selected from the group consisting of a carboxyl group and a C₁-C₄ alkoxy carbonyl group, Y is selected from the group consisting of a hydroxyl group, an acetoxy group and a tetrahydropyranyloxy group and n is an integer of 5 to 7.

2. A 3-cyanocyclopentanone derivative having the formula

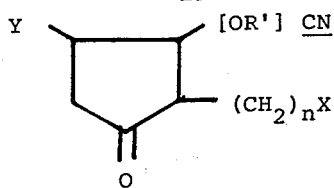

(III)

wherein X is selected from the group consisting of a carboxyl group and a $C_1$-$C_4$ alkoxy carbonyl group, Y is selected from the group consisting of a hydroxyl group, an acetoxy group and a tetrahydropyranyloxy group and $n$ is an integer of 5 to 7.

3. A 3-cyanocyclopentane-1,4-diol derivative having the formula

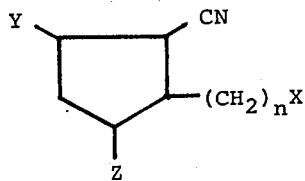

(IV)

wherein X is selected from the group consisting of a carboxyl group and a $C_1$-$C_4$ alkoxy carbonyl group, Y and Z each is selected from the group consisting of a hydroxyl group, an acetoxy group and a tetrahydropyranyloxy group, and $n$ is an integer of from 5 to 7.

4. A process for the production of a 3-cyanocyclopentenone derivative having the formula

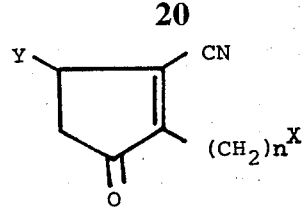

(IV)

wherein X is a carboxy group, a $C_1$-$C_4$ alkoxycarbonyl group or an amido group; Y is a hydroxy group, an acetoxy group or a tetrahydropyranyloxy group; and $n$ is an integer of 5 to 7; which comprises reacting under a cooling to room temperature up to the reflex temperature of any inert solvent used a cyclopentadione enol ether derivative having the formula:

(III)

wherein X, Y and $n$ are as defined above and R' is a lower alkyl group; with 2 to 3 times the molar amount of said ether derivative of a metal salt of hydrocyanic acid together with an ammonium salt of a strong acid or acetone cyanohydrine in the presence of a basic catalyst or hydrocyanic acid activated by a trialkylaluminum or a dialkylcyanoaluminum compound in an inert solvent.

\* \* \* \* \*